United States Patent
Takahata et al.

(10) Patent No.: US 10,646,859 B2
(45) Date of Patent: May 12, 2020

(54) METHOD FOR PRODUCING IRON COMPLEXES AND METHOD FOR PRODUCING ESTER COMPOUNDS USING IRON COMPLEX

(71) Applicant: KURARAY CO., LTD., Kurashiki-shi (JP)

(72) Inventors: Yusuke Takahata, Kurashiki (JP); Tsuyoshi Kajiyashiki, Tsukuba (JP); Tomoya Hosoki, Tsukuba (JP); Kimio Okada, Kurashiki (JP)

(73) Assignee: KURARAY CO., LTD., Kurashiki-shi (JP)

( * ) Notice: Subject to any disclaimer, the term of this patent is extended or adjusted under 35 U.S.C. 154(b) by 0 days.

(21) Appl. No.: 16/312,715

(22) PCT Filed: Jun. 20, 2017

(86) PCT No.: PCT/JP2017/022617
§ 371 (c)(1),
(2) Date: Dec. 21, 2018

(87) PCT Pub. No.: WO2018/003587
PCT Pub. Date: Jan. 4, 2018

(65) Prior Publication Data
US 2019/0351401 A1    Nov. 21, 2019

(30) Foreign Application Priority Data

Jun. 27, 2016 (JP) .................. 2016-126513
Jun. 27, 2016 (JP) .................. 2016-126514
Dec. 26, 2016 (JP) .................. 2016-251074

(51) Int. Cl.
*B01J 31/22* (2006.01)
*C07C 67/03* (2006.01)
(Continued)

(52) U.S. Cl.
CPC .......... *B01J 31/2217* (2013.01); *C07C 67/03* (2013.01); *C07C 69/602* (2013.01);
(Continued)

(58) Field of Classification Search
None
See application file for complete search history.

(56) References Cited

U.S. PATENT DOCUMENTS

2009/0169484 A1   7/2009   Eguchi et al.
2012/0029167 A1   2/2012   Ishikawa et al.
2016/0193337 A1   7/2016   Eguchi et al.

FOREIGN PATENT DOCUMENTS

CN   104327125 A   2/2015
JP   55-143935 A   11/1980
(Continued)

OTHER PUBLICATIONS

Lionel Salmon et al., Two Novel Iron (II) Materials Based on Dianionic $N_4O_2$ Schiff Bases: Structural Properties and Spin-Crossover Characteristics in the Series [Fe(3-X,5-$NO_2$—sal-N(1,4,7,10)] (X=H, 3-MeO. 3-EtO), Inorganic Chemistry, 2005, vol. 44, pp. 1763-1773.

*Primary Examiner* — Clinton A Brooks
(74) *Attorney, Agent, or Firm* — Oblon, McClelland, Maier & Neustadt, L.L.P.

(57) ABSTRACT

Disclosed herein is method for producing an iron dinuclear complex having two iron atoms bonded to each other via one oxygen atom and a ligand structure containing a Schiff base, a method which can produce an ester compound in high yield by the transesterification of an alcohol compound with a carboxylate ester even in the case where the raw material alcohol has a tertiary hydroxyl group which is usually difficult to esterify by transesterification, and a method
(Continued)

which can produce a wholly esterified compound by transesterification catalyzed by an iron complex.

17 Claims, 1 Drawing Sheet

(51) Int. Cl.
    *C07C 69/602*     (2006.01)
    *C07F 15/02*     (2006.01)

(52) U.S. Cl.
    CPC ......... *C07F 15/025* (2013.01); *B01J 2231/49* (2013.01); *B01J 2531/842* (2013.01)

(56) References Cited

FOREIGN PATENT DOCUMENTS

| | | |
|---|---|---|
| JP | 2002-226678 A | 8/2002 |
| JP | 2009-173631 | 8/2009 |
| WO | WO 2010/058280 A1 | 5/2010 |

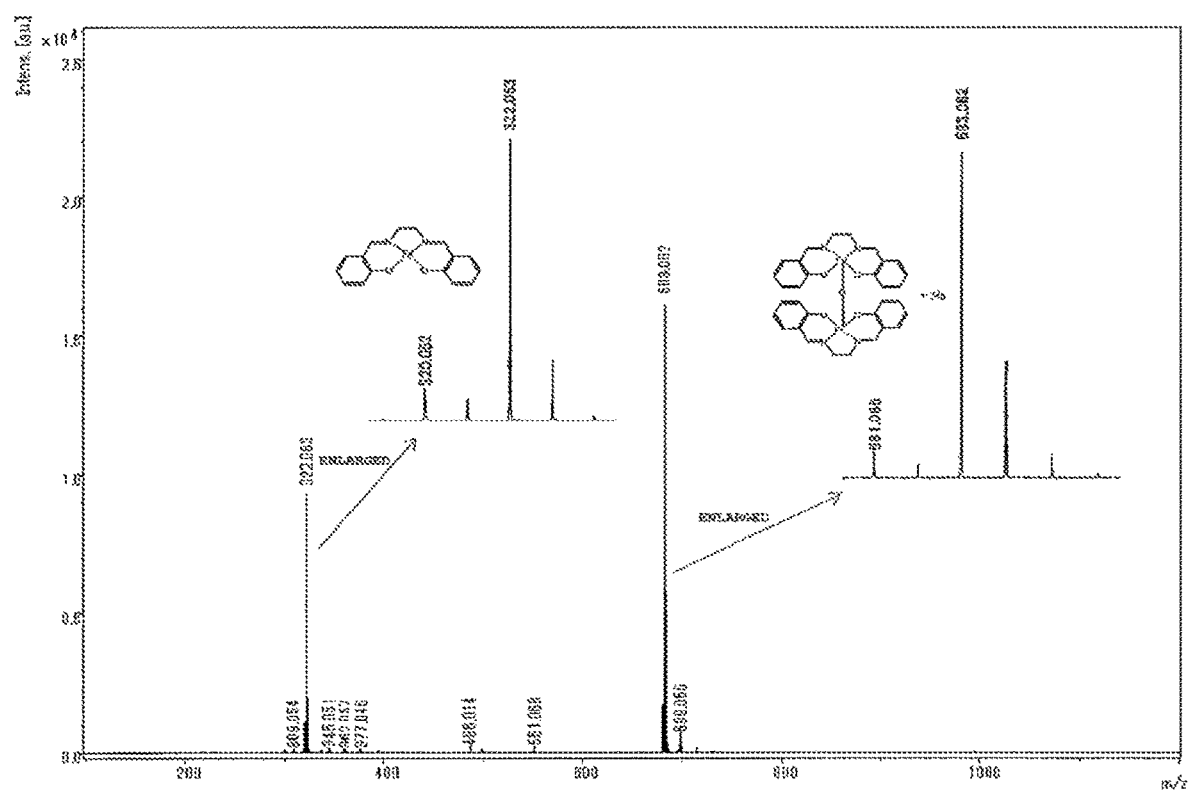

METHOD FOR PRODUCING IRON COMPLEXES AND METHOD FOR PRODUCING ESTER COMPOUNDS USING IRON COMPLEX

TECHNICAL FIELD

The present invention relates to a simple and high-yield method for producing an iron complex which has, in its molecule, a structure having two iron atoms bonded to each other via one oxygen atom and a ligand structure containing a Schiff base. The present invention also relates to a method for producing an ester compound by the transesterification between a carboxylate ester and an alcohol compound catalyzed by an iron complex. More particularly, the invention relates to a method for producing an ester compound by the transesterification between a carboxylate ester and an alcohol compound using an iron complex catalyst produced simply with a high yield and having high activity.

BACKGROUND ART

Iron complexes which have, in the molecule thereof, a Schiff base-containing ligand structure and an iron atom have been conventionally used in industry as additives for resins, pharmaceuticals and catalysts. Some known iron complexes which have a Schiff base-containing ligand structure and an iron atom in the molecule are: iron complexes which have a Schiff base-containing ligand structure and one iron atom in the molecule (hereinafter, such complexes will be referred to as iron mononuclear complexes); and iron complexes which have, in the molecule thereof, a structure having two iron atoms bonded to each other via one oxygen atom and a ligand structure containing a Schiff base (hereinafter, such complexes will be referred to as iron dinuclear complexes). Iron dinuclear complexes outperform iron mononuclear complexes in some applications. When, for example, these iron complexes are used as additives in epoxy resin compositions, the iron dinuclear complexes allow the compositions to exhibit higher flame retardance and higher fluidity than the compositions containing the iron mononuclear complexes. Further, when the iron complexes are used as magnetic carriers for drug delivery systems such as anticancer drugs, the iron dinuclear complexes are known to have high magnetic properties and be suited as carriers compared to the iron mononuclear complexes.

Numerous methods for producing iron dinuclear complexes have been heretofore presented. For example, Patent Literature 1 describes a method for producing an iron dinuclear complex for use as a catalyst wherein salicylaldehyde, ethylenediamine and ferrous sulfate heptahydrate are dissolved into water, the solution is heated, and the resultant black brown precipitate of reaction product is recrystallized from pyridine/ethanol solvent to give [Fe($C_{16}H_{14}N_2O_2$)]$_2$O.

Patent Literature 2 describes a method for producing an iron dinuclear complex for use as an additive for enhancing the flame retardance and fluidity of epoxy resin compositions. Specifically, it is described that salicylaldehyde, ethylenediamine and iron sulfate are dissolved into pure water, and the solution is allowed to stand at 110° C. for 3 hours, cooled and filtered to give an iron dinuclear complex.

Patent Literature 3 describes a method for producing an iron dinuclear complex for use as a magnetic carrier for a drug delivery system such as anticancer drug. Specifically, it is described that a ligand synthesized from a salicylaldehyde derivative and ethylenediamine, and triethylamine are dissolved into methanol, the resultant solution is combined with a methanol solution of ferric chloride, and the resultant compound is washed and recrystallized as an iron dinuclear complex.

As known in the art, the transesterification between a carboxylate ester and an alcohol compound is conventionally performed under catalysis of an iron complex having, in its molecule, a Schiff base-containing ligand structure and an iron atom.

For example, Patent Literature 1 describes that methyl methacrylate is transesterified with an alcohol compound having a primary hydroxyl group or a secondary hydroxyl group in the presence of an iron catalyst, thereby forming the methacrylate ester compound of the alcohol compound having a primary hydroxyl group or a secondary hydroxyl group.

CITATION LIST

Patent Literature

Patent Literature 1: JP-A-S55-143935
Patent Literature 2: JP-A-2002-226678
Patent Literature 3: JP-A-2009-173631

SUMMARY OF INVENTION

Technical Problem

The production methods described in Patent Literatures 1 and 2 do not specify in detail the reaction conditions such as the procedure for mixing salicylaldehyde, ethylenediamine and the iron salt, and show no evidence such as quantitative analytical data of the iron dinuclear complexes obtained. Further, Patent Literature 1 does not specifically consider the transesterification of an alkyl (meth)acrylate with an alcohol compound having a tertiary hydroxyl group to form the methacrylate ester of the alcohol compound having a tertiary hydroxyl group.

Further, the production method described in Patent Literature 3 will be costly due to the complexity of the steps of synthesizing and isolating the ligand, reacting the ligand with the iron salt, and purifying the product.

Studies by the present inventors have shown that an iron complex synthesized by the conventional method is a mixture of an iron mononuclear complex and an iron dinuclear complex. The present inventors have further found that an iron complex catalyzes transesterification, in particular, the esterification of an alcohol compound having a tertiary hydroxyl group, with higher catalytic activity with increasing proportion of an iron dinuclear complex in the iron complex. The present invention has been completed based on these findings.

In one aspect, the present invention is directed to providing a simple and high-yield method for producing an iron dinuclear complex which has, in its molecule, a structure having two iron atoms bonded to each other via one oxygen atom and a ligand structure containing a Schiff base. Thus, an object of the invention is to provide an inexpensive method for producing an iron complex having a high proportion of such an iron dinuclear complex.

Another object of the invention is to provide an ester compound production method which can produce an ester compound with a high yield by the transesterification of an alcohol compound with a carboxylate ester even in the case where the raw material alcohol has a tertiary hydroxyl group which is usually difficult to be esterified by transesterification. Another object of the invention is to provide an ester compound production method which can produce by transesterification a wholly esterified compound, i.e., can esterify all the hydroxyl groups, with a high yield even in the case where the alcohol compound has a plurality of hydroxyl groups.

Solution to Problem

An aspect of the present invention resides in a method for producing an iron complex represented by the general formula (4) or (5) below, the method comprising:

a step (I-1) of preparing a precursor solution by mixing in the presence of water an iron salt and a compound represented by the following general formula (1), and a step (I-2) of mixing the precursor solution with a compound represented by the following general formula (2) or (3),

[Chem. 1]

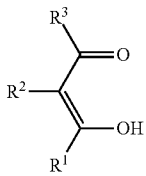
(1)

[Chem. 2]

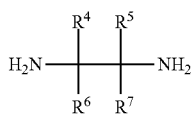
(2)

[Chem. 3]

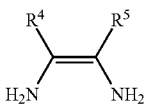
(3)

[Chem. 4]

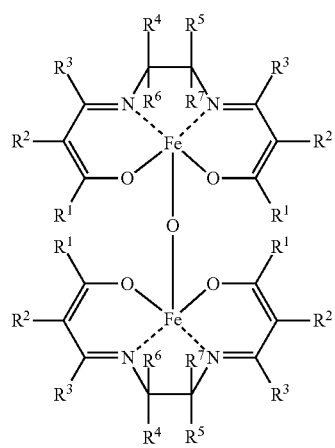
(4)

[Chem. 5]

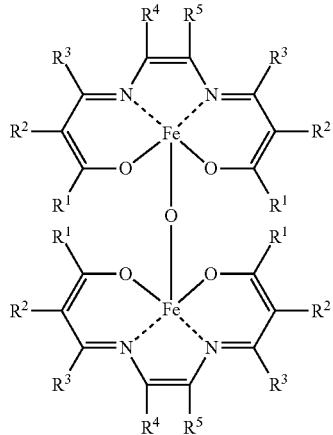
(5)

In the formulae (1), (2), (3), (4) and (5), $R^4$, $R^2$, $R^3$, $R^4$, $R^5$, $R^6$ and $R^7$ are each independently a hydrogen atom, an alkyl group, a monovalent alicyclic group or a monovalent aromatic ring group with the proviso that at least one pair of $R^1$ and $R^2$, $R^2$ and $R^3$, and $R^4$ and $R^5$ may be bonded to each other to form a ring.

In the iron complex production method of the invention, the pH is preferably controlled to above 7 when or after the precursor solution is mixed with the compound represented by the general formula (2) or (3) in the step (I-2).

In the iron complex production method of the invention, the iron salt is preferably trivalent.

In the iron complex production method of the invention, the mixing of the precursor solution and the compound represented by the general formula (2) or (3) in the step (I-2) is preferably performed at a temperature of not less than 50° C.

In the iron complex production method of the invention, the compound represented by the general formula (1) is preferably a compound represented by the following general formula (6), and is more preferably salicylaldehyde.

[Chem. 6]

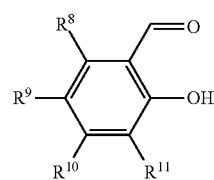
(6)

In the formula (6), $R^8$, $R^9$, $R^{10}$ and $R^{11}$ are each independently a hydrogen atom, an alkyl group, an alkylether group, a halogen atom, a monovalent alicyclic group or a monovalent aromatic ring group with the proviso that at least one pair of $R^8$ and $R^9$, $R^9$ and $R^{10}$, and $R^{10}$ and $R^{11}$ may be bonded to each other to form a ring.

In the iron complex production method of the invention, the compound represented by the general formula (2) is preferably a compound represented by the following general formula (7), and is more preferably ethylenediamine.

[Chem. 7]

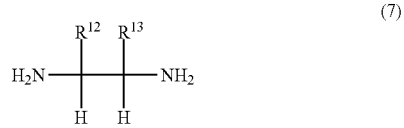

(7)

In the formula (7), $R^{12}$ and $R^{13}$ are each independently a hydrogen atom, an alkyl group, a monovalent alicyclic group or a monovalent aromatic ring group with the proviso that $R^{12}$ and $R^{13}$ may be bonded to each other to form a ring.

According to the present invention, an iron complex represented by the following general formula (8) can be produced.

[Chem. 8]

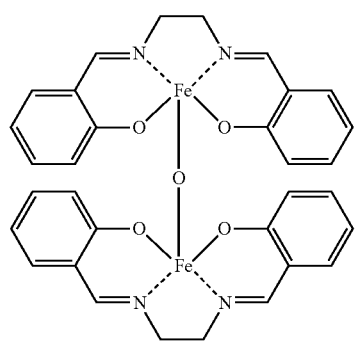

(8)

The iron complex production method of the invention may comprise a step (II) of recovering the iron complex as a solid by filtering a reaction liquid obtained in the step (I-2).

The iron complex production method of the invention may comprise a step (III) of drying the iron complex obtained in the step (II).

According to the present invention, an iron complex catalyst can be produced.

Another aspect of the present invention resides in a method for producing an ester compound comprising a step (IV) of transesterifying a carboxylate ester with an alcohol compound in the presence of an iron complex catalyst produced by the iron complex production method described above.

By virtue of the use of the iron complex as a catalyst, the ester compound production method of the invention can produce a wholly esterified compound with a high yield, in other words, can esterify all the hydroxyl groups present in the alcohol compound even in the case where the alcohol compound has a tertiary hydroxyl group.

In the ester compound production method of the invention, the water content in a reaction system where the transesterification is performed is preferably not more than 1000 ppm.

In the ester compound production method of the invention, the iron complex is preferably used as a catalyst in an amount corresponding to 0.1 to 20 mol % iron atoms relative to the hydroxyl groups in the alcohol compound.

Advantageous Effects of Invention

According to the iron complex production method of the invention, an iron dinuclear complex which has, in its molecule, a structure having two iron atoms bonded to each other via one oxygen atom and a ligand structure containing a Schiff base can be produced simply with a high yield.

The ester compound production method of the invention, by virtue of the use as a catalyst of an iron complex produced simply with a high yield, can produce an ester compound with a high yield even in the case where the raw material alcohol compound has a tertiary hydroxyl group which is usually difficult to be esterified by transesterification. Further, the use of the iron complex as a catalyst makes it possible to produce a wholly esterified compound with a high yield, i.e., to esterify all the hydroxyl groups even in the case where the alcohol compound has a plurality of hydroxyl groups such as tertiary hydroxyl groups.

BRIEF DESCRIPTION OF DRAWING

FIG. 1 is an example of the mass spectrum measured in Test Example 1.

DESCRIPTION OF EMBODIMENTS

The present invention will be described in detail hereinbelow. In the present specification, an iron complex which has, in its molecule, a structure having two iron atoms bonded to each other via one oxygen atom and a ligand structure containing a Schiff base will be sometimes written as "iron dinuclear complex". Further, an iron complex which has a Schiff base-containing ligand structure and one iron atom in the molecule will be sometimes written as "iron mononuclear complex".

The iron salt used in the present invention is not particularly limited and may be any of known salts. Examples of the iron salts include ferrous salts such as ferrous chloride, ferrous sulfate and ferrous nitrate; and ferric salts such as ferric chloride, ferric sulfate, ferric nitrate, basic ferric acetate and iron diethyldithiocarbamate. These iron salts may contain water of crystallization present in their crystals. To enhance the yield of an iron dinuclear complex, ferric salts having trivalent iron (trivalent iron salts) are preferable.

The compound of the general formula (1) that is used in the present invention is not particularly limited and may be any of known such compounds.

[Chem. 9]

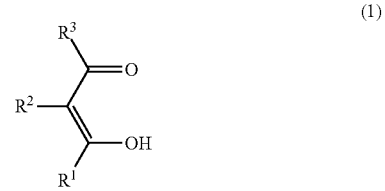

(1)

In the formula (1), $R^1$, $R^2$ and $R^3$ are each independently a hydrogen atom, an alkyl group, a monovalent alicyclic group or a monovalent aromatic ring group. At least one pair of $R^1$ and $R^2$, and $R^2$ and $R^3$ may be bonded to each other to form a ring.

Examples of the rings formed by the bonding of $R^1$ and $R^2$, or $R^2$ and $R^3$ include alicyclic groups and aromatic ring groups. In the alicyclic group, the carbon ring may be a saturated hydrocarbon ring or may include an unsaturated hydrocarbon moiety. The ring in the alicyclic group or the aromatic ring group may be substituted with heteroatoms such as nitrogen atoms, oxygen atoms and sulfur atoms in place of part of the carbon atoms (with the proviso that the ring is not substituted with such heteroatoms continuously).

The monovalent alicyclic group or monovalent aromatic ring group represented by $R^1$, $R^2$ or $R^3$, and the ring formed by the bonding of $R^1$ and $R^2$, or $R^2$ and $R^3$ may have a substituent. Examples of such substituents include halogen groups, hydroxyl groups, alkoxy groups, nitro groups, carboxy groups, formyl groups, acyl groups and sulfonic acid groups.

The compound represented by the formula (1) may be a tautomer represented by the formula (1') or (1") below.

[Chem. 10]

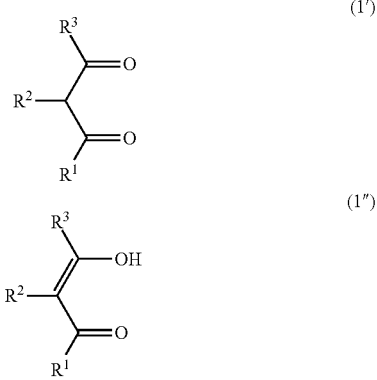

The details such as definitions of $R^1$, $R^2$ and $R^3$ in the formulae (1') and (1") are the same as those of $R^1$, $R^2$ and $R^3$ in the formula (1).

Of the compounds represented by the general formula (1), those compounds represented by the general formula (6) below are preferable in order to enhance the yield of the iron complex.

[Chem. 11]

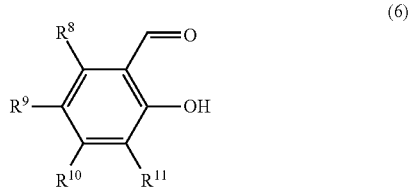

In the formula (6), $R^8$, $R^9$, $R^{10}$ and $R^{11}$ are each independently a hydrogen atom, an alkyl group, an alkylether group, a halogen atom, a monovalent alicyclic group or a monovalent aromatic ring group. At least one pair of $R^8$ and $R^9$, $R^9$ and $R^{10}$, and $R^{11}$ may be bonded to each other to form a ring.

Examples of the rings formed by the bonding of $R^8$ and $R^9$, $R^9$ and $R^{10}$, or $R^{10}$ and $R^{11}$ include alicyclic groups and aromatic ring groups. In the alicyclic group, the carbon ring may be a saturated hydrocarbon ring or may include an unsaturated hydrocarbon moiety. The ring in the alicyclic group or the aromatic ring group may be substituted with heteroatoms such as nitrogen atoms, oxygen atoms and sulfur atoms in place of part of the carbon atoms (with the proviso that the ring is not substituted with such heteroatoms continuously).

The monovalent alicyclic group or monovalent aromatic ring group represented by $R^8$, $R^9$, $R^{10}$ or $R^{11}$, and the ring formed by the bonding of $R^8$ and $R^9$, $R^9$ and $R^{10}$, or $R^{10}$ and $R^{11}$ may have a substituent. Examples of such substituents include halogen groups, hydroxyl groups, alkoxy groups, nitro groups, carboxy groups, formyl groups, acyl groups and sulfonic acid groups.

Examples of the compounds represented by the general formula (1) include carbocyclic or heterocyclic aromatic compounds having an acyl group and a hydroxyl group on adjacent carbon atoms on the ring, such as salicylaldehyde, 2-hydroxy-3-methylbenzaldehyde, 2-hydroxy-4-methylbenzaldehyde, 2-hydroxy-5-methylbenzaldehyde, 2-hydroxy-3,4,5-trimethylbenzaldehyde, 2-hydroxy-3-isopropylbenzaldehyde, 3-nitrosalicylaldehyde, 4-chlorosalicylaldehyde, 4-bromosalicylaldehyde, 4-iodosalicylaldehyde, 5-chlorosalicylaldehyde, 2,3-dihydroxybenzaldehyde, 2,4-dihydroxybenzaldehyde, 2,3,4-trihydroxybenzaldehyde, 2-hydroxyisophthalaldehyde, 3-formylsalicylic acid, 3-methoxysalicylaldehyde, 3-methoxy-5-nitrosalicylaldehyde, 2-hydroxy-1-naphthaldehyde, 6-nitro-2-hydroxy-1-naphthaldehyde, 1-hydroxy-2-naphthaldehyde, 3-hydroxy-2-naphthaldehyde, 4-chloro-2-hydroxy-1-naphthaldehyde, 2,3-dihydroxy-1-naphthaldehyde, 2,8-dihydroxy-1-naphthaldehyde, 2-hydroxy-5,6,7,8-tetrahydro-1-naphthaldehyde, 3-hydroxy-4-formylpyridine, pyridoxal, 4-hydroxyquinoline-3-carboxaldehyde, 7-hydroxyquinoline-8-carboxaldehyde, o-hydroxyacetophenone, 2-hydroxy-3-methylacetophenone, 2-hydroxy-4-methylacetophenone, 2,3-dihydroxyacetophenone, 2-hydroxy-4-methoxyacetophenone, 2,3,4-trihydroxyacetophenone, 2,4,6-trihydroxyacetophenone, 2-hydroxypropiophenone, 2,4-diacetylphenol, 2-hydroxybenzophenone, 5-chloro-2-hydroxyacetophenone, 1-acetyl-2-hydroxynaphthalene, 2-acetyl-1-hydroxynaphthalene, 1-hydroxy-2-propionylnaphthalene, 1-benzoyl-2-hydroxynaphthalene and 2-acetyl-4-chloro-1-hydroxynaphthalene;

compounds having a 1,3-diketone skeleton such as acetylacetone, 2,4-hexadione, 3-methyl-2,4-pentanedione, 2,4-heptanedione, 2,4-nonanedione, 2-acetylcyclohexanone, benzoylacetone, 1,3-diphenyl-1,3-propanedione, 1-(2-furyl)-1,3-butanedione, 1-(2-thienyl)-1,3-butanedione, 1-(2-pyridyl)-1,3-butanedione, 5,9,13,17-tetramethyl-2,4-octadecanedione, 2-(2-methylcaproyl)-cyclopentanone, 2,4,6-heptanetrione and dehydroacetic acid; and α,β-unsaturated carbonyl compounds having a hydroxyl group at the β-position, such as 3-hydroxypropenal, 3-hydroxy-2-methylpropenal, 2,3-dihydroxypropenal, 4-hydroxy-3-buten-2-one and 4-hydroxy-3-penten-2-one. Of these compounds, preferred compounds are those represented by the general formula (6) such as salicylaldehyde, 2-hydroxy-3-methylbenzaldehyde, 2-hydroxy-4-methylbenzaldehyde, 2-hydroxy-5-methylbenzaldehyde, 2-hydroxy-3,4,5-trimethylbenzaldehyde, 2-hydroxy-3-isopropylbenzaldehyde, 3-nitrosalicylaldehyde, 4-chlorosalicylaldehyde, 4-bromosalicylaldehyde, 4-iodosalicylaldehyde, 5-chlorosalicylaldehyde, 2,3-dihydroxybenzaldehyde, 2,4-dihydroxybenzaldehyde, 2,3,4-trihydroxybenzaldehyde, 2-hydroxyisophthalaldehyde, 3-formylsalicylic acid, 3-methoxysalicylaldehyde, 3-methoxy-5-nitrosalicylaldehyde, 2-hydroxy-1-naphthaldehyde, 6-nitro-2-hydroxy-1-naphthaldehyde, 1-hydroxy-2-naphthaldehyde, 3-hydroxy-2-naphthaldehyde, 4-chloro-2-hydroxy-1-naphthaldehyde, 2,3-hydroxy-1-naphthaldehyde, 2,8-dihydroxy-1-naphthaldehyde and 2-hydroxy-5,6,7,8-tetrahydro-1-naphthaldehyde. Salicylaldehyde is more preferable.

The compound of the general formula (2) that is used in the present invention is not particularly limited and may be any of known such compounds.

[Chem. 12]

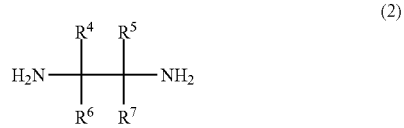

(2)

In the formula (2), $R^4$, $R^5$, $R^6$ and $R^7$ are each independently a hydrogen atom, an alkyl group, a monovalent alicyclic group or a monovalent aromatic ring group. $R^4$ and $R^5$ may be bonded to each other to form a ring.

Examples of the rings formed by the bonding of $R^4$ and $R^5$ include alicyclic groups and aromatic ring groups. In the alicyclic group, the carbon ring may be a saturated hydrocarbon ring or may include an unsaturated hydrocarbon moiety. The ring in the alicyclic group or the aromatic ring group may be substituted with heteroatoms such as nitrogen atoms, oxygen atoms and sulfur atoms in place of part of the carbon atoms (with the proviso that the ring is not substituted with such heteroatoms continuously).

The monovalent alicyclic group or monovalent aromatic ring group represented by $R^4$, $R^5$, $R^6$ or $R^7$, and the ring formed by the bonding of $R^4$ and $R^5$ may have a substituent. Examples of such substituents include halogen groups, hydroxyl groups, alkoxy groups, nitro groups, carboxy groups, formyl groups, acyl groups and sulfonic acid groups.

Of the compounds represented by the general formula (2), those compounds represented by the general formula (7) below are preferable in order to enhance the yield of the iron dinuclear complex.

[Chem. 13]

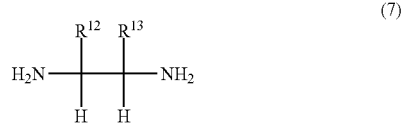

(7)

In the formula (7), $R^{12}$ and $R^{13}$ are each independently a hydrogen atom, an alkyl group, a monovalent alicyclic group or a monovalent aromatic ring group. $R^{12}$ and $R^{13}$ may be bonded to each other to form a ring.

Examples of the rings formed by the bonding of $R^{12}$ and $R^{13}$ include alicyclic groups and aromatic ring groups. In the alicyclic group, the carbon ring may be a saturated hydrocarbon ring or may include an unsaturated hydrocarbon moiety. The ring in the alicyclic group or the aromatic ring group may be substituted with heteroatoms such as nitrogen atoms, oxygen atoms and sulfur atoms in place of part of the carbon atoms (with the proviso that the ring is not substituted with such heteroatoms continuously).

The monovalent alicyclic group or monovalent aromatic ring group represented by $R^{12}$ or $R^{13}$, and the ring formed by the bonding of $R^{12}$ and $R^{13}$ may have a substituent. Examples of such substituents include halogen groups, hydroxyl groups, alkoxy groups, nitro groups, carboxy groups, formyl groups, acyl groups and sulfonic acid groups.

Examples of the compounds represented by the general formula (2) include ethylenediamine, and ethylenediamine derivatives such as 1,2-diaminopropane, 1,2-diaminobutane, 2,3-diaminobutane, 1,1,2,2-tetramethylethylenediamine, 1,1,2-trimethylethylenediamine and 1-phenylethyldiamine. Of these compounds, preferred compounds are those represented by the general formula (7) such as ethylenediamine, 1,2-diaminopropane, 1,2-diaminobutane, 2,3-diaminobutane and 1-phenylethyldiamine. Ethylenediamine is more preferable.

The compound of the general formula (3) that is used in the present invention is not particularly limited and may be any of known such compounds.

[Chem. 14]

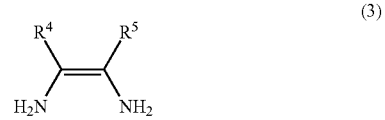

(3)

The details such as definitions of $R^4$ and $R^5$ in the formula (3) are the same as those of $R^4$ and $R^5$ in the formula (2).

Examples of the compounds represented by the general formula (3) include diamines having two amino groups on adjacent carbon atoms in an aromatic ring, such as o-phenylenediamine, 4-methyl-o-phenylenediamine, 4-nitro-o-phenylenediamine, 2,3-diaminonaphthalene, 2,3-diaminopyridine, 2,3-diaminopyrazine, 3,4-diaminopyrazine and 2,3-diaminofuran.

An iron dinuclear complex produced by the iron complex production method of the present invention is a compound represented by the general formula (4) or (5) below. Such an iron complex may be used as, for example, a catalyst (an iron complex catalyst) in synthesis such as an ester compound production method of the present invention.

[Chem. 15]

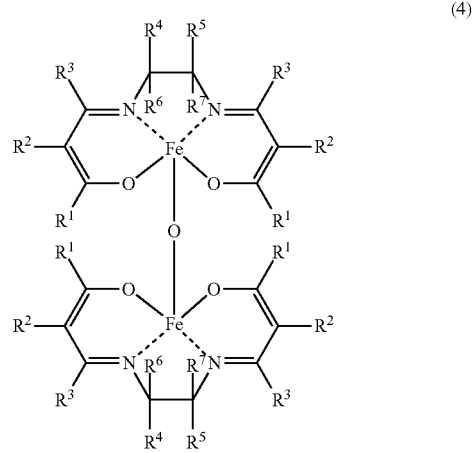

(4)

[Chem. 16]

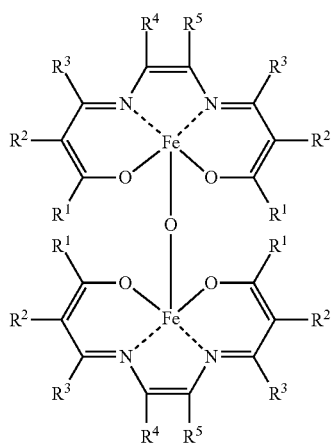

(5)

[Chem. 17]

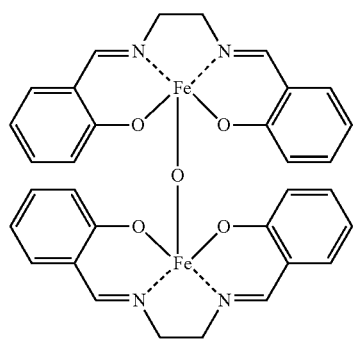

(8)

In the formulae (4) and (5), $R^1$, $R^2$, $R^3$, $R^4$, $R^5$, $R^6$ and $R^7$ are each independently a hydrogen atom, an alkyl group, a monovalent alicyclic group or a monovalent aromatic ring group. At least one pair of $R^1$ and $R^2$, $R^2$ and $R^3$, and $R^4$ and $R^5$ may be bonded to each other to form a ring.

Examples of the rings formed by the bonding of $R^1$ and $R^2$, $R^2$ and $R^3$, or $R^4$ and $R^5$ include alicyclic groups and aromatic ring groups. In the alicyclic group, the carbon ring may be a saturated hydrocarbon ring or may include an unsaturated hydrocarbon moiety. The ring in the alicyclic group or the aromatic ring group may be substituted with heteroatoms such as nitrogen atoms, oxygen atoms and sulfur atoms in place of part of the carbon atoms (with the proviso that the ring is not substituted with such heteroatoms continuously).

The monovalent alicyclic group or monovalent aromatic ring group represented by $R^1$, $R^2$, $R^3$, $R^4$, $R^5$, $R^6$ or $R^7$, and the alicyclic group or aromatic ring group formed by the bonding of $R^1$ and $R^2$, $R^2$ and $R^3$, or $R^4$ and $R^5$ may have a substituent. Examples of such substituents include halogen groups, hydroxyl groups, alkoxy groups, nitro groups, carboxy groups, formyl groups, acyl groups and sulfonic acid groups.

The iron complex of the present invention may be bonded to a carrier, a low-molecular compound or the like through the above substituent to attain an enhancement in convenience in the industrial use of the complex as, for example, an additive for resins, a pharmaceutical or a catalyst. When the iron complex is used as a catalyst in the ester compound production method of the present invention, the complex may be bonded to a carrier or the like through the above substituent to attain an enhancement in convenience in the use of the catalyst.

According to the iron complex production method of the present invention, an iron dinuclear complex represented by the following general formula (8) may be produced from salicylaldehyde, ethylenediamine and iron salt as raw materials.

The iron complex production method of the invention includes a step of synthesizing an iron complex (hereinafter, sometimes written simply as the "step (I)") in which an iron salt and a compound represented by the aforementioned general formula (1) are mixed together beforehand in the presence of water to give a precursor solution (step (I-1)), and thereafter the precursor solution obtained in the step (I-1) and a compound represented by the aforementioned general formula (2) or (3) are mixed together (step (I-2)) to form an iron complex. That is, the step (I-1) is typically performed in the absence of the compound represented by the general formula (2) or (3). In this manner, the proportion of an iron dinuclear complex relative to an iron mononuclear complex may be increased, and consequently the target iron dinuclear complex may be produced with a high yield. If the synthesis is performed otherwise, for example, (i) if an iron salt, a compound represented by the general formula (1) and a compound represented by the general formula (2) or (3) are mixed together at once in the presence of water; (ii) if a solution of a mixture of a compound represented by the general formula (1) and a compound represented by the general formula (2) or (3) is mixed together with an iron salt in the presence of water; or (iii) if a solution of a mixture of an iron salt and a compound represented by the general formula (2) or (3) is mixed together with a compound represented by the general formula (1) in the presence of water, the coordination of iron to the ligand compounds does not proceed due to problems such as the precipitation of the ligand compounds, and consequently the yield of the iron dinuclear complex is significantly reduced.

Studies by the present inventors have revealed that the oxygen atom used in the formation (dinucleation) of an iron dinuclear complex, that is, the oxygen atom in the iron atom-oxygen atom-iron atom bond originates from water contained in the reaction system. Thus, the reaction system in the step (I), especially the reaction system in the step (I-2), should contain water. Water may be supplied as a solvent (for example, water or a water-containing organic solvent) used in the reaction in the step (I). Water may be also supplied as water of crystallization present in the iron salt.

The organic solvent is not particularly limited, and use maybe made of known organic solvents. In particular, alcohols such as methanol and ethanol are preferable because such organic solvents are capable of dissolving the iron salt, the compound of the general formula (1), the compound of the general formula (2) or (3) and water.

For reasons such as that the iron complex that is formed is insoluble in water and therefore the reaction can be driven to an end by precipitation, that the product can be easily recovered in a step (II), and that the waste disposal load can be reduced, the source which supplies water in the reaction system in the step (I), especially water in the reaction system in the step (I-2), is preferably water exclusively used as the solvent in the reaction in the step (I).

In the step (I-2), the pH is preferably controlled to above 7 (the liquid is preferably rendered basic) when or after the precursor solution obtained in the step (I-1) is mixed with the compound represented by the general formula (2) or (3). The pH is more preferably controlled to 9 or above, and still more preferably to 10 or above. When the pH is in this range, the yield of the iron dinuclear complex may be increased. If, on the other hand, the liquid is neutral or acidic, the yield of the iron dinuclear complex tends to be lowered. The pH may be controlled by adding a basic compound. Examples of the basic compounds include organic basic compounds such as the compounds of the general formula (2) or (3) which are the reaction substrates, triethylamine, pyridine and triethanolamine; and inorganic basic compounds such as sodium hydroxide, sodium hydrogen carbonate and ammonia.

In the step (I-2), the mixing of the precursor solution obtained in the step (I-1) and the compound represented by the general formula (2) or (3) is preferably performed at a temperature of not less than 50° C., more preferably 50° C. to 100° C., and most preferably 60° C. to 80° C. If the temperature is below 50° C., the reaction proceeds hardly and the yield of the iron dinuclear complex is lowered. If the temperature is high (for example, above 100° C.), heating costs tend to be increased.

In the step (I-1), there is no limitation on the amount of time for which the iron salt and the compound of the general formula (1) are mixed together in the presence of water to give a precursor solution. To obtain an iron dinuclear complex with a high yield, the mixing of the precursor solution and the compound of the general formula (2) or (3) in the step (I-2) is preferably performed for 10 minutes to 4 hours, and more preferably 30 minutes to 3 hours. If this amount of time in the step (I-2) is less than 10 minutes, the yield of the iron dinuclear complex tends to be lowered. If the amount of time exceeds 4 hours, increased fixed production costs tend to be incurred.

The molar ratio of the starting materials in the production method of the invention, namely, the molar ratio of the iron salt to the compound represented by the general formula (1) may be selected appropriately in consideration of factors such as economic efficiency, but is usually 1:0.5 to 1:10, preferably 1:1 to 1:4, and more preferably 1:2 to 1:3. The molar ratio of the iron salt to the compound represented by the general formula (2) or (3) may be selected appropriately in consideration of factors such as economic efficiency, but is usually 1:1 to 1:10, preferably 1:1 to 1:5, and more preferably 1:2 to 1:5.

The reaction liquid from the step (I) which includes the iron complex may be subjected to a step (II) in which the liquid is filtered to remove undesired components such as unreacted raw materials and to recover the iron complex as a solid. The filtration method is not particularly limited and may be conventional. Specific examples of the filtration methods include pressure filtration, suction filtration and centrifugation.

Further, the iron complex obtained in the step (II) may be subjected to a step (III) in which it is dried. The drying method is not particularly limited and may be conventional. Specific examples of the drying methods include vacuum drying, hot air drying and freeze drying.

The mechanism as to why the iron complex production method of the present invention can produce an iron dinuclear complex with a high yield is unclear but is probably as estimated below. A complex is usually synthesized by producing a desired ligand and allowing a salt containing a metal to act on the ligand. An iron salen complex is usually produced by mixing all the raw materials, namely, a hydroxyl-containing organic acid, a diamine derivative and an iron salt. In this case, it is believed that the hydroxyl-containing organic acid and the diamine derivative quickly undergo dehydration condensation to form a ligand, and thereafter the iron salt acts on the ligand to form an iron salen complex.

The size of a site where a ligand and a metal are bonded together is sterically limited by the ligand. Thus, in the case of an iron salen complex, the number of water molecules hydratable to an iron salt that is bonded to a ligand composed of a hydroxyl-containing organic acid and a diamine derivative will be limited by the size of a bonding site of the ligand. After studies based on these estimations, it is assumed that the premixing of a hydroxyl-containing organic acid and an iron salt results in a precursor which does not sterically limit the number of water molecules hydratable to the iron salt forming the precursor.

More specifically, in the production of an iron salen complex from the above precursor, it is assumed that the iron salt is hydrated with a larger number of water molecules than the number of water molecules hydrated to an iron salt in the case where an iron salen complex is produced by the conventional production method. Because the oxygen which constitutes the bridge in the target iron dinuclear complex of the present invention originates from water as the reaction solvent, it is assumed that the method of the present invention which allows more water molecules to hydrate to the iron salt will facilitate the formation of an iron dinuclear complex.

The iron complexes produced by the iron complex production method of the present invention may be used in any applications without limitation, such as additives for resins, pharmaceuticals and catalysts. Particularly, the iron complexes are preferably used as catalysts (iron complex catalysts).

In the method for producing ester compounds according to the present invention, an ester compound is produced by a step (IV) of transesterifying a carboxylate ester with an alcohol compound in the presence of an iron complex (a catalyst) of the general formula (4) or (5) that is obtained through steps including the above-described step (I). The transesterification using the iron complex as a catalyst may be performed in any manner without limitation. For example, the reaction may be performed by mixing the carboxylate ester, the alcohol compound and the catalyst, and heating the mixture. The reaction may be promoted by distilling away the alcohol byproduct derived from the carboxyl ate ester. The iron complex may be immobilized on a carrier through a substituent. The immobilization to a carrier facilitates the separation of the catalyst from the reaction liquid.

The carboxylate ester used in the transesterification is not particularly limited and may be any of known such compounds. For the reason that the alcohol which is byproduced in the reaction can be distilled away easily, a compound having a lower alkyl group such as methyl, ethyl, n-propyl, iso-propyl, n-butyl, iso-butyl or t-butyl as the ester group is preferable. Examples of the carboxylate esters include methyl acetate, ethyl acetate, n-propyl acetate, iso-propyl acetate, n-butyl acetate, methyl acrylate, ethyl acrylate, n-propyl acrylate, iso-propyl acrylate, n-butyl acrylate, methyl methacrylate, ethyl methacrylate, n-propyl methacrylate, iso-propyl methacrylate and n-butyl methacrylate.

The alcohol compound used in the transesterification is not particularly limited and may be any of known such compounds. Because the iron dinuclear complex obtained in the present invention has high catalytic activity, tertiary hydroxyl groups can be particularly efficiently esterified. The alcohol compounds having a tertiary hydroxyl group may be monohydric alcohols or polyhydric alcohols. Examples of the monohydric alcohols include t-butyl alcohol, t-amyl alcohol and 2-methyl-3-buten-2-ol. Examples of the polyhydric alcohols include isoprene glycol, 4-methyl-2,4-pentanediol, 5-methyl-3,5-hexanediol, 6-methyl-4,6-heptanediol, 7-methyl-5,7-octanediol, 4-methyl-1,4-pentanediol, 5-methyl-1,5-hexanediol, 6-methyl-1,6-heptanediol, 3-methyl-1,3-pentanediol, 3-methyl-1,3-hexanediol, 3-propyl-1,3-hexanediol, 3-ethyl-1,3-heptanediol, 3-methyl-1,3-nonanediol, 4-methyl-1,4-hexanediol, 5-methyl-1,5-heptanediol and 6-methyl-1,6-octanediol.

Further, the high catalytic activity of the iron dinuclear complex obtained in the present invention allows all the hydroxyl groups present in the raw material alcohol compound to be esterified by the acyl groups present in the raw material carboxylate ester with good efficiency in the step (IV). Examples of such compounds resulting from the esterification of all the hydroxyl groups present in the alcohol compound include t-butyl acetate, t-butyl methacrylate and isoprene glycol dimethacrylate.

In the transesterification in the step (IV), the alcohol compound, in particular, the alcohol compound having a tertiary hydroxyl group tends to be esterified at a higher rate and the yield tends to be increased with decreasing water content in the reaction system. Thus, the water content in the reaction system (the reaction liquid) where the transesterification is performed in the step (IV) is preferably not more than 1000 ppm, more preferably not more than 600 ppm, and still more preferably not more than 100 ppm. If the reaction system contains more than 1000 ppm water, the transesterification activity with respect to tertiary hydroxyl groups tends to be lowered, and the reaction is often prolonged, is often accompanied by side reactions, and often results in a low yield.

The water content in the reaction system in the step (IV) may be kept low in any manner without limitation as long as the water content in the reaction system can be maintained at the desired low level. Unlike titanium alcoholates which are known transesterification catalysts, the transesterification catalysts including the iron dinuclear complexes described hereinabove are not decomposed and deactivated by water. Therefore, the dehydration of the reaction system may take place before the reaction or after the start of the reaction. Some example approaches to keeping low the water content in the reaction system are to azeotropically remove water contained in the raw materials before the reaction by the use of a solvent that is azeotropic with water; to add a solvent azeotropic with water to the reaction system and perform the reaction while azeotropically evaporating water; and to use a desiccant such as molecular sieve to adsorb and remove beforehand water contained in the raw materials. In particular, it is preferable that the transesterification in the step (IV) be preceded by a step in which the catalyst including the iron dinuclear complex to be used in the transesterification in the step (IV) is dehydrated beforehand. Specifically, such a dehydration step may be performed in such a manner that the catalyst including the iron dinuclear complex is dehydrated with use of an azeotropic solvent in the presence of the alcohol compound. The azeotropic solvent may be any known solvent which does not hinder reactions such as transesterification, with examples including toluene, xylene, 2-butanone, dioxane, benzene and cyclohexane.

When the reaction is performed under total reflux, the water content in the reaction system may be kept low by, for example, passing the condensate through a column packed with a desiccant such as molecular sieve so as to adsorb and remove water.

In the transesterification in the step (IV), the molar ratio of the hydroxyl groups in the starting material alcohol compound to the acyl groups in the starting material carboxylate ester is selected appropriately in consideration of factors such as economic efficiency, boiling point and azeotropic properties. The ratio of the number of moles of the hydroxyl groups in the alcohol compound to the number of moles of the acyl groups in the carboxylate ester is usually 1:1 to 1:50, and preferably 1:1 to 1:20.

In the ester compound production method of the present invention, the iron dinuclear complex (the iron complex catalyst) is usually used in an amount corresponding to 0.1 to 20 mol % iron atoms relative to the hydroxyl groups in the alcohol compound (where the alcohol contains a plurality of hydroxyl groups, the total number of hydroxyl groups). The amount preferably corresponds to 0.5 to 15 mol % iron atoms, and more preferably corresponds to 1 to 10 mol % iron atoms. Using an excessively larger amount of the catalyst raises the cost too much. If the amount is excessively small, the reaction is so prolonged that the productivity tends to be deteriorated.

In the transesterification in the step (IV), the reaction temperature is usually 70 to 150° C., preferably 80 to 120° C., and more preferably 90 to 110° C. The reaction time is extended and the productivity is lowered with decreasing reaction temperature. Too high a reaction temperature increases the risk of side reactions. The reaction pressure may be atmospheric, but may be reduced to facilitate the removal of the alcohol formed. From the point of view of productivity, the reaction time is usually not more than 200 hours, preferably not more than 150 hours, and more preferably not more than 100 hours.

The transesterification in the step (IV) may involve a solvent. The solvent may be any of known solvents except those which undergo side reactions with compounds such as alcohol compounds and carboxylate ester compounds or which inhibit reactions such as transesterification. The solvent may be selected appropriately in consideration of factors such as azeotropic properties with water and by-produced alcohols, and reaction temperature. Examples of the solvents include toluene, xylene, 2-butanone, dioxane, benzene and cyclohexane.

The reaction liquid obtained from the transesterification in the step (IV) may be further subjected to a distillation step in which undesired components such as unreacted raw materials are removed. Examples of the distillation methods include thin-film distillation and packed column distillation.

When, for example, the compounds which are used in the transesterification in the step (IV) are polymerizable, it is preferable to add a polymerization inhibitor and/or to introduce oxygen into the reaction system for the purpose of preventing the polymerization. The polymerization inhibitor may be any of known such substances without limitation, and may be, for example, anyone or a combination of hydroquinone, hydroquinone monomethyl ether, di-t-butylhydroxytoluene, phenothiazine and N,N'-dinaphthyl-p-phenylenediamine.

EXAMPLES

Hereinbelow, the present invention will be described in greater detail by presenting Examples and Comparative Examples. However, it should be construed that the scope of the invention is not limited to such Examples.

The analyses in Examples and Comparative Examples were performed in accordance with Test Examples 1 and 2 below.

(Test Example 1) Ratio of Iron Dinuclear Complex 0.5 g of a powder obtained in Example or Comparative Example and 0.5 g of sodium chloride were added to a mortar and were ground to give a mixture. A portion of the mixture was placed onto MALDI target plate, and a small amount of ion exchanged water was added. Thereafter, water was evaporated. A measurement sample was thus prepared. A mass spectrum of the measurement sample was recorded using MALDI-TOF-MS (manufactured by Bruker). The mass spectrum obtained was analyzed to determine the intensities of the peak of an iron mononuclear complex (m/z=322) and the peak of an iron dinuclear complex (m/z=683), and thereby the ratio (%) of the iron dinuclear complex=Iron dinuclear complex/(Iron mononuclear complex+Iron dinuclear complex)×100 was calculated.

The mass spectrum of the iron complex is shown in FIG. 1.

(Test Example 2) Transesterification Catalytic Performance

A 50 mL three-necked flask that had been equipped with a column having a side tube and packed with 20 g of molecular sieve (4A), a condenser, a thermometer and a drying tube was loaded with 0.64 g of an iron complex (the mass was that of a powder obtained in Example or Comparative Example), 1.04 g of isoprene glycol, 40 g of methyl methacrylate, 0.08 g of phenothiazine and 0.2 g of tridecane. While performing stirring under atmospheric pressure, the flask was soaked into an oil bath set at 120° C. so that the inside temperature of the flask would be 100 to 105° C. The reaction was performed for 7 hours while returning all the condensed fractions to the reaction system through the molecular sieve.

The reaction liquid was sampled, filtered and analyzed by gas chromatography. Using tridecane as an inner standard, isoprene glycol dimethacrylate was quantitatively determined. The transesterification catalytic performance was evaluated by determining the yield (mol %) of isoprene glycol dimethacrylate relative to the raw material isoprene glycol taken as 100 mol %. By a Karl Fischer moisture measurement method, the amount of water in the fractions being returned to the reaction system through the molecular sieve was measured, and thereby the water content in the reaction liquid in this test system was determined to be 0.1 ppm.

(Gas Chromatography Conditions)

Apparatus: GC-2014 (manufactured by Shimadzu Corporation)
Column: DB-1, 0.25 mm φ×30 mm, film thickness 0.25 μm (manufactured by Agilent)
Injection temperature: 280° C.
Column temperature: Held at 50° C. for 5 minutes, raised to 280° C. at 10° C./min, and held constant for 3 minutes.
FID detector temperature: 280° C.
Carrier gas: helium, column flow rate 1.5 mL/min
Injection volume: 0.2 μL
(Karl Fischer moisture measurement conditions)
Apparatus: CA-100 (manufactured by Mitsubishi Chemical Corporation)
Anolyte: AQUAMICRON AX (manufactured by Mitsubishi Chemical Corporation)
Catholyte: AQUAMICRON CXU (manufactured by Mitsubishi Chemical Corporation)
Injection volume: 0.2 g

Example 1

A 1 L four-necked flask equipped with a condenser tube, a dropping funnel, a thermometer and a mechanical stirrer was loaded with 750 mL of water. 112 g (0.28 mol) of ferric nitrate nonahydrate was added thereto and dissolved. 68 g (0.56 mol) of salicylaldehyde was added dropwise to the solution, and the mixture was stirred at room temperature for 30 minutes to give a black precursor solution. Subsequently, 50 g (0.83 mol) of ethylenediamine was added dropwise to the precursor solution. After the completion of the dropwise addition, the mixture was heated and stirred at an inner temperature of 70° C. for 2 hours. Further, 11 g (0.18 mol) of ethylenediamine was added, and the mixture was stirred at an inner temperature of 70° C. for 2 hours to give a yellow brown suspension. The pH of the suspension was checked with pH test paper to be 10. The suspension was suction filtered, and the residue was washed with water until the pH of the filtrate became 7 to 8. The solid thus obtained was vacuum dried at 120° C. Consequently, 87 g of a yellow powder was obtained. The yield, and the results of the evaluations of the powder in accordance with Test Examples 1 and 2 are shown in Table 1.

Example 2

A 200 mL four-necked flask equipped with a condenser tube, a dropping funnel, a thermometer and a mechanical stirrer was loaded with 120 mL of water. 16.2 g (0.040 mol) of ferric nitrate nonahydrate was added thereto and dissolved. 9.8 g (0.080 mol) of salicylaldehyde was added dropwise to the solution, and the mixture was stirred at room temperature for 30 minutes to give a black precursor solution. Subsequently, 6.0 g (0.10 mol) of ethylenediamine was added dropwise to the precursor solution. After the completion of the dropwise addition, the mixture was heated and stirred at an inner temperature of 60° C. for 2 hours to give a yellow brown suspension. The pH of the suspension was checked with pH test paper to be 7. The suspension was suction filtered, and the residue was washed with water. The solid thus obtained was vacuum dried at 120° C. Consequently, 11.6 g of a yellow powder was obtained. The yield, and the results of the evaluations of the powder in accordance with Test Examples 1 and 2 are shown in Table 1.

Example 3

A 200 mL four-necked flask equipped with a condenser tube, a dropping funnel, a thermometer and a mechanical stirrer was loaded with 120 mL of water. 11.1 g (0.040 mol) of ferrous sulfate heptahydrate was added thereto and dissolved. 9.8 g (0.080 mol) of salicylaldehyde was added dropwise to the solution, and the mixture was stirred at room temperature for 30 minutes to give a black precursor solution. Subsequently, 4.8 g (0.080 mol) of ethylenediamine was added dropwise to the precursor solution. After the completion of the dropwise addition, the mixture was heated and stirred at an inner temperature of 60° C. for 2 hours. Further, 3.6 g (0.060 mol) of ethylenediamine was added, and the mixture was stirred at an inner temperature of 70° C. for 2 hours to give a yellow brown suspension. The pH of the suspension was checked with pH test paper to be 10. The suspension was suction filtered, and the residue was washed with water until the pH of the filtrate became 7 to 8. The solid thus obtained was vacuum dried at 120° C. Consequently, 11.9 g of a yellow powder was obtained. The yield, and the results of the evaluations of the powder in accordance with Test Examples 1 and 2 are shown in Table 1.

Example 4

A 200 mL four-necked flask equipped with a condenser tube, a dropping funnel, a thermometer and a mechanical stirrer was loaded with 120 mL of water. 11.1 g (0.040 mol) of ferrous sulfate heptahydrate was added thereto and dissolved. 9.8 g (0.080 mol) of salicylaldehyde was added dropwise to the solution, and the mixture was stirred at room temperature for 30 minutes to give a black precursor solution. Subsequently, 4.8 g (0.080 mol) of ethylenediamine was added dropwise to the precursor solution. After the completion of the dropwise addition, the mixture was heated and stirred at an inner temperature of 70° C. for 2 hours to give a yellow brown suspension. The pH of the suspension was checked with pH test paper to be 7. The suspension was suction filtered, and the residue was washed with water. The solid thus obtained was vacuum dried at 120° C. Consequently, 11.5 g of a yellow powder was obtained. The yield, and the results of the evaluations of the powder in accordance with Test Examples 1 and 2 are shown in Table 1.

Comparative Example 1

A 200 mL four-necked flask equipped with a condenser tube, a dropping funnel, a thermometer and a mechanical stirrer was loaded with 120 mL of water. At room temperature, 11.1 g (0.040 mol) of ferrous sulfate heptahydrate, 9.8 g (0.080 mol) of salicylaldehyde and 4.8 g (0.080 mol) of ethylenediamine were added. The mixture was heated and was stirred at an inner temperature of 60° C. for 2 hours to give a red brown suspension. The pH of the suspension was checked with pH test paper to be 7. The suspension was suction filtered, and the residue was washed with water. The solid thus obtained was vacuum dried at 120° C. Consequently, 8.6 g of a red brown powder was obtained. The yield, and the results of the evaluations of the powder in accordance with Test Examples 1 and 2 are shown in Table 1.

Comparative Example 2

A 200 mL four-necked flask equipped with a condenser tube, a dropping funnel, a thermometer and a mechanical stirrer was loaded with 120 mL of water. At room temperature, 16.2 g (0.040 mol) of ferric nitrate nonahydrate, 9.8 g (0.080 mol) of salicylaldehyde and 7.2 g (0.12 mol) of ethylenediamine were added. The mixture was heated and was stirred at an inner temperature of 70° C. for 2 hours to give a brown suspension. Further, 1.8 g (0.03 mol) of ethylenediamine was added, and the mixture was stirred at an inner temperature of 70° C. for 2 hours to give a brown suspension. The pH of the suspension was checked with pH test paper to be 10. The suspension was suction filtered, and the residue was washed with water until the pH of the filtrate became 7 to 8. The solid thus obtained was vacuum dried at 120° C. Consequently, 8.8 g of a brown powder was obtained. The yield, and the results of the evaluations of the powder in accordance with Test Examples 1 and 2 are shown in Table 1.

Comparative Example 3

A 200 mL four-necked flask equipped with a condenser tube, a dropping funnel, a thermometer and a mechanical stirrer was loaded with 120 mL of water. At room temperature, 9.8 g (0.080 mol) of salicylaldehyde and 7.2 g (0.12 mol) of ethylenediamine were added. The mixture was stirred at room temperature for 1 hour to give a yellow white suspension. Further, 16.2 g (0.040 mol) of ferric nitrate nonahydrate was added, and the mixture was stirred at an inner temperature of 70° C. for 2 hours to give a black brown suspension. Further, 1.8 g (0.03 mol) of ethylenediamine was added, and the mixture was stirred at an inner temperature of 70° C. for 2 hours to give a brown suspension. The pH of the suspension was checked with pH test paper to be 10. The suspension was suction filtered, and the residue was washed with water until the pH of the filtrate became 7 to 8. The solid thus obtained was vacuum dried at 120° C. Consequently, 8.1 g of a red brown powder was obtained. The yield, and the results of the evaluations of the powder in accordance with Test Examples 1 and 2 are shown in Table 1.

TABLE 1

|  | Examples | | | | Comparative Examples | | |
|---|---|---|---|---|---|---|---|
|  | 1 | 2 | 3 | 4 | 1 | 2 | 3 |
| Yield (%) (calculated in terms of iron dinuclear complex based on the amount of iron salt) | 94 | 88 | 90 | 87 | 65 | 67 | 62 |
| Ratio (%) of iron dinuclear complex | 85 | 67 | 59 | 46 | 11 | 16 | 13 |
| Transesterification catalytic performance Yield (mol %) of isoprene glycol dimethacrylate | 81 | 68 | 61 | 55 | 29 | 35 | 31 |

The results of Examples and Comparative Examples have shown that an iron complex can be obtained with a high yield and the ratio of an iron dinuclear complex can be increased by preparing beforehand a mixed solution of an aqueous iron salt solution and salicylaldehyde, and mixing the resultant solution with ethylenediamine. Further, it has been shown that the catalysts having an increased ratio of an iron dinuclear complex attain enhanced transesterification catalytic performance and can catalyze the esterification of a tertiary hydroxy compound to provide a high yield.

From the comparison of Examples 1 and 2 or the comparison of Examples 3 and 4, it has been shown that the ratio of an iron dinuclear complex can be increased by rendering the reaction system basic.

Further, it has been shown from the comparison of Examples 1 and 3 or the comparison of Examples 2 and 4 that the ratio of an iron dinuclear complex can be increased by using a trivalent iron salt as a raw material.

INDUSTRIAL APPLICABILITY

The iron complex production method of the present invention can produce simply with a high yield an iron dinuclear complex which has, in its molecule, a structure having two iron atoms bonded to each other via one oxygen atom and a ligand structure containing a Schiff base. Thus, the iron complex production method of the present invention is useful for industrial mass production of iron dinuclear complexes valuable as additives for resins, pharmaceuticals and catalysts.

Further, the ester compound production method of the present invention uses as a catalyst an iron dinuclear complex that is produced simply with a high yield and has, in its molecule, a structure having two iron atoms bonded to each other via one oxygen atom and a ligand structure containing a Schiff base. By virtue of the use of such a catalyst, the ester compound production method of the present invention can produce an ester compound with a high yield even in the case where the raw material alcohol compound has a tertiary hydroxyl group which is difficult to be esterified by transesterification, and the production method can also produce a wholly esterified compound resulting from the esterification of all the hydroxyl groups with a high yield even in the case where the alcohol compound has a plurality of hydroxyl groups.

Thus, the ester compound production method of the present invention is useful for industrial scale production of tertiary ester compounds and ester compounds of polyhydric alcohols, and can overcome difficulties conventionally encountered in the mass synthesis of such ester compounds.

The invention claimed is:

1. A method for producing an iron complex represented by the general formula (4) or (5) below,

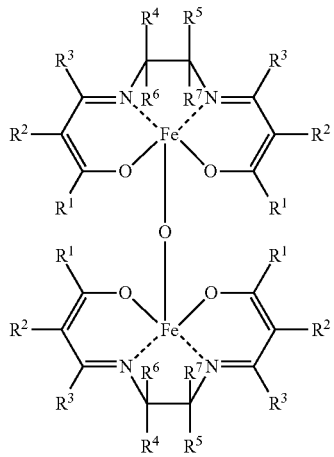
(4)

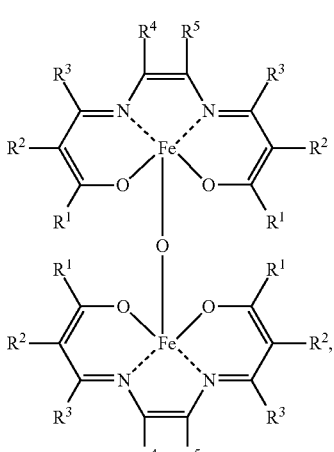
(5)

the method comprising:
(I-1) mixing in the presence of water an iron salt and a compound represented by formula (1), to obtain a precursor solution:

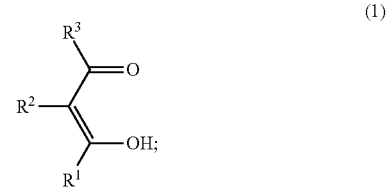
(1)

and
a step (I-2) mixing the precursor solution with a compound represented by formula (2) or (3):

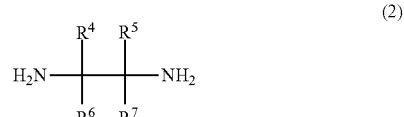
(2)

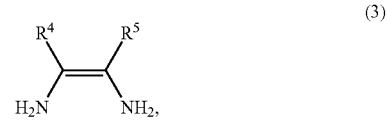
(3)

wherein:
$R^1$, $R^2$, $R^3$, $R^4$, $R^5$, $R^6$ and $R^7$ are each independently a hydrogen atom, an alkyl group, a monovalent alicyclic group or a monovalent aromatic ring group,
with the proviso that at least one pair of $R^1$ and $R^2$, $R^2$ and $R^3$, and $R^4$ and $R^5$ may be bonded to each other to form a ring.

2. The iron complex production method according to claim 1, wherein pH is controlled to above 7 when or after the precursor solution is mixed with the compound represented by the general formula (2) or (3) in the step (I-2).

3. The iron complex production method according to claim 1, wherein the iron salt is trivalent.

4. The iron complex production method according to claim 1, wherein the mixing of the precursor solution and the compound represented by the general formula (2) or (3) in the step (I-2) is performed at a temperature of not less than 50° C.

5. The iron complex production method according to claim 1, wherein the compound represented by the formula (1) is a compound represented by formula (6):

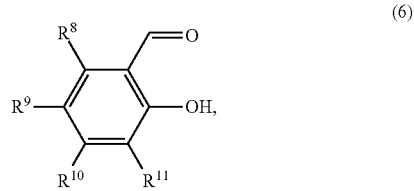
(6)

wherein:
$R^8$, $R^9$, $R^{10}$ and $R^{11}$ are each independently a hydrogen atom, an alkyl group, an alkylether group, a halogen atom, a monovalent alicyclic group or a monovalent aromatic ring group, with the proviso that at least one pair of $R^8$ and $R^9$, $R^9$ and $R^{10}$, and $R^{10}$ and $R^{11}$ may be bonded to each other to form a ring.

6. The iron complex production method according to claim 1, wherein the compound represented by the formula (2) is a compound represented by formula (7):

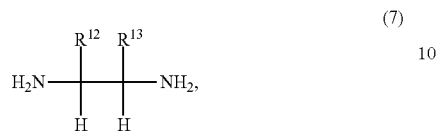

wherein:
$R^{12}$ and $R^{13}$ are each independently a hydrogen atom, an alkyl group, a monovalent alicyclic group or a monovalent aromatic ring group,
with the proviso that $R^{12}$ and $R^{13}$ may be bonded to each other to form a ring.

7. The iron complex production method according to claim 1, wherein the compound represented by the formula (1) is salicylaldehyde.

8. The iron complex production method according to claim 1, wherein the compound represented by the formula (2) is ethylenediamine.

9. The iron complex production method according to claim 1, wherein the iron complex represented by the formula (4) is an iron complex represented by formula (8):

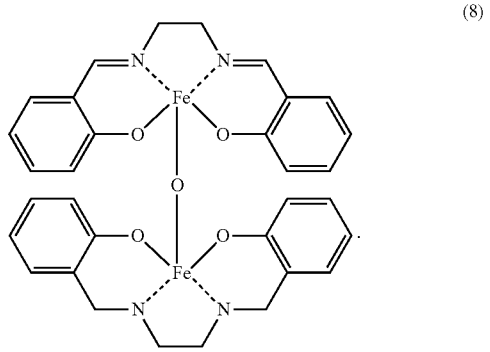

10. The iron complex production method according to claim 1, further comprising:
(II) recovering the iron complex as a solid by filtering a reaction liquid obtained in the step (I-2).

11. The iron complex production method according to claim 10, further comprising:
(III) drying the iron complex obtained in the step (II).

12. The iron complex production method according to claim 1, wherein the iron complex is an iron complex catalyst.

13. A method for producing an ester compound, the method comprising:
(IV) transesterifying a carboxylate ester with an alcohol compound in the presence of an iron complex produced by the iron complex production method of claim 12.

14. The ester compound production method according to claim 13, wherein the alcohol compound subjected to the transesterifying step (IV) is a compound having a tertiary hydroxyl group.

15. The ester compound production method according to claim 13, wherein the ester compound obtained in the step (IV) is a wholly esterified compound resulting from esterification of all the hydroxyl groups in the alcohol compound by the acyl groups in the carboxylate ester.

16. The ester compound production method according to claim 13, wherein a water content in a reaction system where the transesterifying is performed in the step (IV) is not more than 1000 ppm.

17. The ester compound production method according to claim 13, wherein, in the transesterifying in the step (IV), the iron complex is present in an amount corresponding to 0.1 to 20 mol % iron atoms relative to the hydroxyl groups in the alcohol compound.

* * * * *